United States Patent
Zhang

(10) Patent No.: US 10,603,293 B2
(45) Date of Patent: *Mar. 31, 2020

(54) SOLID-FORMING LOCAL ANESTHETIC FORMULATIONS FOR PAIN CONTROL

(71) Applicant: Crescita Therapeutics Inc., Mississauga (CA)

(72) Inventor: Jie Zhang, Salt Lake City, UT (US)

(73) Assignee: Crescita Therapeutics Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,417

(22) Filed: Jun. 14, 2018

(65) Prior Publication Data

US 2018/0289644 A1 Oct. 11, 2018

Related U.S. Application Data

(63) Continuation of application No. 15/613,695, filed on Jun. 5, 2017, now Pat. No. 10,350,180, which is a continuation of application No. 13/006,780, filed on Jan. 14, 2011, now Pat. No. 9,693,976.

(60) Provisional application No. 61/294,927, filed on Jan. 14, 2010.

(51) Int. Cl.
| | | |
|---|---|---|
| A61K 31/167 | (2006.01) | |
| A61K 9/00 | (2006.01) | |
| A61K 31/136 | (2006.01) | |
| A61K 47/32 | (2006.01) | |

(52) U.S. Cl.
CPC .......... *A61K 31/167* (2013.01); *A61K 9/0014* (2013.01); *A61K 31/136* (2013.01); *A61K 47/32* (2013.01)

(58) Field of Classification Search
USPC ...................................................... 514/537
See application file for complete search history.

(56) References Cited

U.S. PATENT DOCUMENTS

| | | |
|---|---|---|
| 3,929,131 A | 12/1975 | Hardwick |
| 4,230,105 A | 10/1980 | Harwood |
| 4,286,592 A | 9/1981 | Chandrasekaran |
| 4,529,601 A | 7/1985 | Broberg et al. |
| 4,685,911 A | 8/1987 | Konno et al. |
| 4,693,706 A | 9/1987 | Ennis, III |
| 4,695,465 A | 9/1987 | Kigasawa et al. |
| 4,747,841 A | 5/1988 | Kuratomi et al. |
| 4,780,320 A | 10/1988 | Baker |
| 4,830,855 A | 5/1989 | Stewart |
| 4,879,119 A | 11/1989 | Konno et al. |
| 4,898,592 A | 2/1990 | Latzke et al. |
| 4,911,707 A | 3/1990 | Heiber et al. |
| 4,913,957 A | 4/1990 | Strack et al. |
| 4,963,360 A | 10/1990 | Argaud |
| 4,994,049 A | 2/1991 | Latzke et al. |
| 5,108,710 A | 4/1992 | Little et al. |
| 5,114,411 A | 5/1992 | Haber et al. |
| 5,128,137 A | 7/1992 | Muller et al. |
| 5,147,339 A | 9/1992 | Sundstrom |
| 5,213,129 A | 5/1993 | Someah et al. |
| 5,217,718 A | 6/1993 | Colley et al. |
| 5,229,133 A | 7/1993 | Wright et al. |
| 5,276,032 A | 1/1994 | King et al. |
| 5,279,594 A | 1/1994 | Jackson |
| 5,329,976 A | 7/1994 | Haber et al. |
| 5,330,452 A | 7/1994 | Zook |
| 5,364,350 A | 11/1994 | Dittmann |
| 5,370,879 A | 12/1994 | Masterson et al. |
| 5,378,730 A | 1/1995 | Lee et al. |
| 5,658,583 A | 8/1997 | Zhang et al. |
| 5,733,572 A | 3/1998 | Unger et al. |
| 5,776,952 A | 7/1998 | Liedtke |
| 5,840,755 A | 11/1998 | Liedtke |
| 5,885,597 A | 3/1999 | Botknecht et al. |
| 5,906,814 A | 5/1999 | Epstein |
| 5,919,479 A | 7/1999 | Zhang et al. |
| 5,993,836 A | 11/1999 | Castillo |
| 6,036,966 A | 3/2000 | Youssefyeh |
| 6,211,250 B1 | 4/2001 | Tomlinson et al. |
| 6,245,347 B1 | 6/2001 | Zhang et al. |
| 6,261,595 B1 | 7/2001 | Stanley et al. |
| 6,324,424 B1 | 11/2001 | Ledger et al. |
| 6,453,648 B1 | 9/2002 | Zhang |

(Continued)

FOREIGN PATENT DOCUMENTS

| | | |
|---|---|---|
| DE | 2851369 | 6/1979 |
| EP | 0386960 | 9/1990 |

(Continued)

OTHER PUBLICATIONS

Unknown, Local Anesthetics, https://web.archive.org/web/20120906202800/http://www.ifna-int.org/ifna/e107_files/downloads/lectures/H1LocalAne.pdf, downloaded Aug. 11, 2014, 20 pages.

Unknown, Types of Polymers, https://web.archive.org/web/20070712124323/http://chemed.chem.purdue.edu/genchem/topicreview/bp/1polymer/types.html, downloaded Aug. 12, 2014, 7 pages.

Saupe, Biological Polymers: Proteins, Carbohydrates, Lipids & Nucleic Acids, Introduction to Cell & Molecular Biology (BIOL121), https://web.archive.org/web/20081116091144/http://employees.csbsju.edu/SSAUPE/biol121/chem_biol.html, downloaded Aug. 12, 2014, 4 pages.

Astra USA, Inc., EMLA Cream (lidocaine 2.5% and prilocaine 2.5%), Product Information Form for American Hospital Formulary Service, 1993, 27 pages.

(Continued)

*Primary Examiner* — Marcos L Sznaidman
(74) *Attorney, Agent, or Firm* — Thorpe North & Western, LLP

(57) ABSTRACT

Solid-forming local anesthetic formulations for pain control can include a lidocaine base and tetracaine base, polyvinyl alcohol, water, and an emulsifier. The formulation can be prepared to be in a semi-solid state prior to application to a skin surface, can form a soft solidified layer after application, and can provide pain relief when applied to a skin surface proximate a pain site.

14 Claims, No Drawings

(56) References Cited

U.S. PATENT DOCUMENTS

| | | | |
|---|---|---|---|
| 6,465,709 | B1 | 10/2002 | Sun et al. |
| 6,488,959 | B2 | 12/2002 | Stanley et al. |
| 6,528,086 | B2 | 3/2003 | Zhang |
| 6,756,053 | B2 | 6/2004 | Zhang et al. |
| 6,756,426 | B2 | 6/2004 | Brother et al. |
| 6,955,819 | B2 | 10/2005 | Zhang et al. |
| 7,063,859 | B1 | 6/2006 | Kanios et al. |
| 2002/0004063 | A1* | 1/2002 | Zhang ............ A61K 9/0034 424/443 |
| 2005/0075407 | A1 | 4/2005 | Tamarkin et al. |
| 2005/0209319 | A1 | 9/2005 | Cundy |
| 2005/0232957 | A1 | 10/2005 | Katz |
| 2005/0239868 | A1 | 10/2005 | Shirai et al. |
| 2005/0276842 | A1 | 12/2005 | Zhang et al. |
| 2006/0147510 | A1 | 7/2006 | Galer |
| 2007/0059351 | A1 | 3/2007 | Murrell et al. |
| 2007/0068508 | A1 | 3/2007 | York-Leung Wong |
| 2007/0189978 | A1 | 8/2007 | Zhang |
| 2007/0196323 | A1 | 8/2007 | Zhang et al. |
| 2007/0196458 | A1 | 8/2007 | Zhang et al. |
| 2007/0299540 | A1 | 12/2007 | Ku |
| 2008/0021051 | A1 | 1/2008 | Wilson |
| 2008/0260655 | A1 | 10/2008 | Tamarkin et al. |
| 2010/0273838 | A1 | 10/2010 | Cui et al. |
| 2011/0015229 | A1 | 1/2011 | Zhang et al. |

FOREIGN PATENT DOCUMENTS

| | | |
|---|---|---|
| EP | 0455396 | 11/1991 |
| EP | 0770387 | 5/1997 |
| EP | 2163956 | 3/2010 |
| GB | 2163959 | 3/1986 |
| JP | 62051617 | 3/1987 |
| JP | 5279018 | 10/1993 |
| WO | 8809169 | 12/1988 |
| WO | 9213529 | 8/1992 |
| WO | 9619453 | 6/1996 |
| WO | 9715548 | 5/1997 |
| WO | 9738675 | 10/1997 |
| WO | 9922717 | 5/1999 |
| WO | 0018339 | 4/2000 |
| WO | 0122907 | 4/2001 |
| WO | 2004000358 | 12/2003 |
| WO | 2005120473 | 12/2005 |
| WO | 2007070679 | 6/2007 |
| WO | 2008150995 | 12/2008 |
| WO | 2009053572 | 4/2009 |
| WO | 2010080831 | 7/2010 |
| WO | 2010114973 | 10/2010 |
| WO | 2010129542 | 11/2010 |
| WO | 2011088333 | 7/2011 |
| WO | 2012080831 | 6/2012 |

OTHER PUBLICATIONS

Cada et al., Lidocaine/Tetracaine Patch, Formulary Drug Reviews, Hospital Pharmacy, vol. 41, No. 3, 2006 Wolters Kluwer Health, Inc., pp. 265-273.

Hoshino et al., Preparation of a Local Anaesthetic Ointment Containing the Eutectic Mixture of Lidocaine and Tetracaine, Yakuzalgaku, 1991, abstract only.

Kawano et al., Comparison of analgesic effect of lidocaine tape versus eutectic mixture of lidocaine and tetracaine during infiltration of local anesthetics before epidural block, PubMed, 1996, abstract only.

Knutson et al., Solvent-Medicated Alterations of the Stratum Corneum, Journal of Controlled Release, 11, 1990, pp. 93-103.

Lycka, EMLA A New and Effective Topical Anesthetic, J Dermatol Sug Oncol, 1992, pp. 859-862.

Mack Publishing Company, Stability of Pharmaceutical Products, 1985, pp. 1481-1482.

McCafferty et al., Comparative In Vivo and In Vitro Assessment of the Percutaneous Absorption of Local Anaesthetics, Br. J. Anaesth., 1988, p. 64-69.

McCafferty et al., In Vivo Assessment of Percutaneous Local Anaesthetic Preparations, Br. J. Anaesth, 1989, pp. 17-21.

McCafferty et al., New Patch Delivery System for Percutaneous Local Anaesthesia, British Journal of Anaesthesia, 1993, pp. 370-374.

Ohzeki et al., Local Anesthetic Cream Prepared from Lidocaine-Tetracaine Eutectic Mixture, Yakugaku Zasshi 128 (4), 2008, pp. 611-616.

Risovic et al., Formulacija I Ispitivanje Rubefacijentnog Dejstva Preparata Sa Kapsaicinom, Lek. Sirov, vol. XXI, No. 21, 2001, pp. 157-161.

Sakamoto et al., Dermal patch anaesthesia: comparison of 10% lignocaine gel with absorption promotor and EMLA cream, Anaesthesia, vol. 48, 1993, pp. 390-392.

Woolfson et al., Concentration-Response Analysis of Percutaneous Local Anaesthetic Formulations, Br. J. Anaesth., vol. 61, 1988, pp. 589-592.

Woolfson, Percutaneous Local Anaesthesia, Formulation of local anaesthetics for percutaneous deliver, Ch. 5, 1993, pp. 166-170.

Yap, Myofascial Pain—An Overview, Annals Academy of Medicine, vol. 36, No. 1, 2007, pp. 43-48.

Young, What's New in Topical Anesthesia, Clinical Pediatric Emergency Medicine, 2007, pp. 232-239.

Argoff, A Review of the Use of Topical Analgesics for Myofascial Pain, Current Pain and Headach Reports, 2002, pp. 375-378.

International Search Report and Written Opinion dated Sep. 28, 2011 for PCT/US2011/021318, Applicant Zars Pharma, Inc. et al.

European Search Report dated Jun. 7, 2013 for PCT/US2011/021318, Applicant Nuvo Research Inc.

\* cited by examiner

SOLID-FORMING LOCAL ANESTHETIC FORMULATIONS FOR PAIN CONTROL

The present application is a continuation of U.S. patent application Ser. No. 15/613,695 filed on Jun. 5, 2017, which is a continuation of U.S. patent application Ser. No. 13/006,780, filed on Jan. 14, 2011 (now U.S. Pat. No. 9,693,976), which claims the benefit of U.S. Provisional Patent Application No. 61/294,927, filed Jan. 14, 2010.

BACKGROUND

Non-invasive pain control methods are desirable in treating pain, such as neuropathic pain. It would be useful to provide formulations that are easy to use, have good storage stability, particularly freeze-thaw storage stability, and are effective for non-invasive pain control treatment.

DETAILED DESCRIPTION

Before particular embodiments of the present invention are disclosed and described, it is to be understood that this disclosure is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

"Skin" is defined to include human skin (intact, diseased, ulcerous, or broken), and mucosal surfaces that are usually at least partially exposed to air such as lips, genital and anal mucosa, and nasal and oral mucosa.

The term "solid-forming local anesthetic formulation" or "solid-forming formulation" refers to a formulation that is in the state of a semi-solid and comprises a local anesthetic, water, and a polymer before being applied onto a skin surface. After being applied to a skin surface as a thin layer (e.g., 1 mm thick), the solid-forming local anesthetic formulation forms a layer of a coherent solid after sufficient concentration of water is evaporated from the formulation layer. Examples of semi-solid forms include creams, ointments, pastes, viscous lotions, gels, and the like. It is notable that the solid-forming formulations of the present disclosure are free of backing layers or backing films and are formulated to be applied directly to a skin surface as a semi-solid state without the need of a separate support substrate (e.g. backing layer or backing firm) both before application and after being applied. The ability of the formulation to be applied directly to the skin without a backing layer, backing film, or other support substrate enhances the ability of the formulation to better adhere to regions of a subjects skin that do not readily lend themselves to traditional transdermal patches (i.e. those that include backing layers or backing films). By enhancing adherence to such surfaces, the solid-forming formulations are more effective in delivering therapeutically effective amounts of the local anesthetics, thereby providing enhanced relief of the neuropathic pain.

As used herein, the term "semi-solid" refers to a composition having a viscosity of about 40,000 centipoise to about 800,000 centipoise. As discussed above, compositions having viscosities in this range that can be deemed semi-solids can include creams, ointments, pastes, viscous lotions, gels, and the like. It is notable that not all of the foregoing compositions are considered to be semi-solids, but rather only those that having viscosities that fall within the above range. In one aspect of the disclosure, the semi-solid formulations can have a viscosity of about 70,000 centipoise to about 500,000 centipoise.

The phrases "sufficient amount of water" or "sufficient concentration of water" refers to an amount or a concentration of water evaporated from an applied layer of the formulation such that the formulation transitions from a semi-solid to a coherent solid.

"Coherent solid" or "coherent soft solid" describes the solidified layer of the solid-forming local anesthetic formulation after a sufficient concentration of water has evaporated (sufficient to cause the solidification). The coherent soft solid remains adhered to the skin and is capable of maintaining good contact with the subject's skin for substantially the entire duration of desired application. Additionally, a "coherent solid" can have cohesive strength sufficient such that the solid remains intact when peeled from the skin. In other words, cohesive soft solids do not include dried lotions and other viscous semi-solids that are non-cohesive even after drying but rather, includes compositions that remain at least partially cohesive in the solid state, even after being removed from a skin surface. In one embodiment, the coherent solid can be peelable from the skin, e.g., the coherent solid can remain as a single large piece when peeled from the skin, or tears into 2 or 3 large pieces.

The term "initial state" when used to describe a solid-forming local anesthetic formulation refers to the state of the formulation before being applied to a skin surface. The state of application in the initial state is typically a semi-solid state, e.g., cream, gel, ointment, liquid, etc., and not the coherent solid state, e.g., peelable or otherwise removable solid that coherent as a thin solid layer.

The term "initial viscosity" refers to the viscosity of the formulation at room temperature (typically about 25° C.) prior to a freeze/thaw cycle.

The term "freeze/thaw cycle" refers to the placement of the formulation in an environment having a temperature of −18° C. to −22° C. for a period of time of 48 hours followed by the thawing of the formulation at a temperature of about 25° C. for a period of 48 hours. One freezing and one thawing period together are considered to be one (1) freeze/thaw cycle. It is noted that the temperature range reflects temperature fluctuation associated with the typical cycling of a freezer set to freeze at about −20° C.

The term "neuropathic pain" refers to any and all types of neuropathic pain regardless of the cause. Examples of specific sources of neuropathic pain for which the methods of the present disclosure can be used include diabetic neuropathies and virus-caused neuropathies. The treatment of neuropathic pain as described herein refers to the alleviation or elimination of the neuropathic pain associated with a neuropathy.

The term "proximate" when referring to a location on a skin surface, particularly as it relates to the location of neuropathic pain, means an area of skin directly over (in part or fully covering) or immediately adjacent to tissue from which the neuropathic pain is present.

The phrases "relief of neuropathic pain," "relief of pain," and "clinically relevant reduction of neuropathic pain", and the like, are used interchangeably and are defined as an average reduction of 3 points or more from the baseline on an 11-point numeric pain rating scale compared with placebo when tested using at least 12 subjects.

As used herein, a plurality of drugs, compounds, and/or solvents may be presented in a common list for convenience.

However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

With this background in mind, a formulation for pain control is provided. In one embodiment, the formulation includes lidocaine and tetracaine, each in their base form. The formulation also includes polyvinyl alcohol, water, and an emulsifying agent having an HLB value of less than 6.7. The formulation can have a water to polyvinyl alcohol weight ratio greater than 2.4.

In another embodiment, a formulation for treating neuropathic pain is provided. The formulation includes lidocaine and tetracaine, each in their base form, as well as polyvinyl alcohol, water, petrolatum, and an emulsifying agent. The emulsifying agent has an HBL value of less than 5.

In yet another embodiment, a formulation for providing pain control can comprise lidocaine and tetracaine in their base forms, polyvinyl alcohol, and water. The formulation can have an initial viscosity of about 40,000 centipoise to about 800,000 centipoise, and can have an increase in viscosity after 3 freeze/thaw cycles of less than 8 times the initial viscosity with a maximum viscosity of 1,500,000 centipoise. Each of the 3 freeze/thaw cycles can be determined by placement of the formulation in an environment of −18° C. to −22° C. for a period of time of 48 hours followed by the thawing of the formulation at room temperature (about 25° C.) for a period of 48 hours.

In still another embodiment, a formulation for providing pain control can comprise from 4 wt % to 30 wt % of a eutectic mixture of lidocaine and tetracaine, from 10 wt % to 18 wt % polyvinyl alcohol, from 30 wt % to 50 wt % water, from 2 wt % to 13 wt % petrolatum, and from 2 wt % to 6 wt % sorbitan monostearate. The water to polyvinyl alcohol weight ratio can be greater than 2.4. Also, the formulation cab have an initial viscosity of about 70,000 centipoise to about 500,000 centipoise, and can have an increase in viscosity after 3 freeze/thaw cycles of less than 8 times the initial viscosity with a maximum viscosity of 1,500,000 centipoise. Each of the 3 freeze/thaw cycles can be determined by placement of the formulation in an environment of −18° C. to −22° C. for a period of time of 48 hours followed by the thawing of the formulation at room temperature (about 25° C.) for a period of 48 hours.

Regarding the local anesthetic active ingredients described herein, the present disclosure is drawn primarily to mixtures of lidocaine and tetracaine, typically as a eutectic mixture where each local anesthetic is in its base form. Typically, the mixture of the local anesthetics will be present in total within the composition as a whole at from 4 wt % to 30 wt %, and more typically from 8 wt % to 20 wt %, though any functional concentration can be present at any effective ratio, i.e. lidocaine base to tetracaine base ratio. Typically, the lidocaine to tetracaine base weight ratio can be from 2:1 to 1:2, and is often about 1:1, though ratios outside of this range are often effective as well.

As set forth herein, the formulations of the present disclosure can have initial viscosities of about 40,000 centipoise to about 800,000 centipoise. In one embodiment, the formulation can have a viscosity of about 70,000 centipoise to about 500,000 centipoise. These viscosities allow for the formulations to be readily spread onto skin surfaces without running off. Further, it has been discovered that the formulations of the present disclosure have the unique ability to maintain their viscosities in these ranges after multiple freeze/thaw cycles. This ability provides a significant advantage over previous formulations. Formulations containing both PVA and water frequently experience dramatic increases in viscosity after freeze/thaw cycles. Without being limited by theory, it is believed that the increase in viscosity in these PVA and water containing formulations is due to the tendency of the PVA to cross-link as a result of these cycles. This increase in viscosity is particularly problematic for consumers and practitioners who store the formulations in refrigerators to comply with the storage recommendations for users. As the viscosity of the formulations increases, the formulations become increasingly difficult to expel or remove from their storage containers and to apply and spread onto the skin surface, resulting in unusable and wasted formulations. Because refrigerators in the physicians' offices often reach freezing temperatures (below 0° C.), it is desirable that the formulation can experience freeze/thaw cycles without overly significant increases in viscosity.

Accordingly, in one embodiment of the present disclosure, the formulations have an initial viscosity from about 50,000 centipoise to about 800,000 centipoise, and can have an increase in viscosity after at least 3 freeze/thaw cycles of less than eight (8) times the initial viscosity with a maximum viscosity less than 1,500,000 centipoise. In one embodiment, the increase in viscosity can be less than (5) times the initial viscosity. In another embodiment, the formulations can have an initial viscosity from about 70,000 centipoise to about 500,000 centipoise, and can have an increase in viscosity after at least 3 freeze/thaw cycles of less than five (5) times the initial viscosity with a maximum viscosity of 1,500,000 centipoise. In another embodiment, the formulations can have an initial viscosity from about 70,000 centipoise to about 500,000 centipoise, and can have an increase in viscosity after at least 3 freeze/thaw cycles of less than three (3) times the initial viscosity with a maximum viscosity of 1,500,000 centipoise. In a further embodiment, the formulations of the present disclosure can have an initial viscosity from about 70,000 centipoise to about 500,000 centipoise, and can have an increase in viscosity after at least 4 freeze/thaw cycles of less than three (3) times the initial viscosity with a maximum viscosity of 1,500,000 centipoise. In still another embodiment, the viscosity of the formulation after 3 freeze/thaw cycles does not exceed 1,000,000 centipoise. In yet another embodiment, the viscosity of the formulation after 3 freeze/thaw cycles does not exceed 800,000 centipoise. In yet a further embodiment, the viscosity of the formulation after 3 freeze/thaw cycles does not exceed 500,000 centipoise. Unless otherwise specified, all viscosity values in the current disclosure are generated by the viscosity measurement methodology set forth in Example 1.

It is noted that the reason it is desirable to not exceed 1,500,000 centipoise (and more desirably less than 1,000,000 centipoise or even less) after going through various freeze/thaw cycles is related to the composition becoming difficult to remove from a squeeze tube and apply to a skin surface after it gets much above this level of viscosity. When practitioners refrigerate this material, if the composition becomes inadvertently frozen, if the viscosity is increased too much due to crosslinking of the polyvinyl alcohol, the composition can become virtually unusable. Thus, acceptable freeze/thaw performance as described herein represents a significant advancement in the art as it relates to the specific types of compositions described herein.

Another unique parameter of the formulations of the present disclosure is the weight ratio of water to PVA in the formulation (water/PVA ratio). It has been discovered that formulations having water to PVA ratios above 2.4 have significantly better freeze-thaw performance than those with water/PVA ratio below that threshold. Accordingly, in one embodiment, the formulations of the present disclosure have a water to PVA ratio (W/W) of at least 2.4. In another embodiment, the formulations have a water to PVA ratio (W/W) of at least 2.5. In yet a further embodiment, the formulation can have a water to PVA ratio (W/W) of at least 2.8.

The polyvinyl alcohol present in the formulations of the present disclosure facilitates the transition of the formulations from an initial semi-solid initial state to a solidified state. Accordingly, it is desirable for the formulations to contain concentrations of PVA sufficient to facilitate this conversion. Formulations with excessive PVA concentrations can have high viscosities and be too difficult to apply or spread onto a skin surface. Similarly, formulations with insufficient PVA concentrations can produce undesirably long drying times and poor cohesion of the solidified formulation layer. Accordingly, in one aspect of the present disclosure, the formulation can include 6 wt % to 25 wt % of polyvinyl alcohol. In another aspect of the disclosure, the formulation can include 10 wt % to 18 wt %.

The molecular mass of polyvinyl alcohol in the formulation is also notable in the context of the present disclosure. Used within the concentration ranges described herein, the polyvinyl alcohol's average molecular mass can be in the range of 20,000 to 100,000 Daltons. More typically, the average molecular mass can be in the range of 30,000 to 80,000 Daltons. When lower molecular mass PVA is used in the formulations of the current disclosure, the viscosity of the formulations can be too low for spreading on the skin and the cohesion can be too weak to provide appropriate adherence to the skin. When PVA with meaningfully higher molecular mass is used in the formulations of the present disclosure, the viscosity of the formulations can be too high and the manufacturing of the formulations in large scale can be difficult (higher molecular mass PVAs are more difficult to dissolve). The average molecular mass of PVA used in the formulations of the examples herein is typically in the range of 40,000 to 70,000 Daltons.

The solid-forming local anesthetic formulations of the present disclosure are in an initial semi-solid state before they are applied to a skin surface. After application, the formulations form a soft coherent solid layer after the evaporation of sufficient amount of water. Thus, the formulation starts as a semi-solid. After being applied as a thin layer (0.3-1.0 mm or more), the surface dries to the touch in about 5-30 minutes and later the entire layer solidifies into a coherent soft solid.

The solid-forming local anesthetic formulation can deliver the local anesthetics to the skin and underlying tissues from the moment it is applied on the skin surface until substantially all the water is evaporated from the formulation. Accordingly, the delivery of the local anesthetic agents continues after the formulation transforms into a layer of soft solid, because typically there is still significant amount of water in the formulation layer even after the formulation solidifies. After evaporation of substantially all of the water, delivery of the local anesthetics typically stops or slows significantly, although the therapeutic effect may still be present long after the drug delivery has stopped due to the storage of the local anesthetic agents in the skin, as well as by the mechanical protection provided by the coherent solid remaining on the skin surface. In one embodiment, the formulation can include 30 wt % to 55 wt % water. In another embodiment, formulation can include 35 wt % to 50 wt % water.

The formulations of the present disclosure are, by nature, oil-in-water emulsions and may comprise two or more oil phases. For example, in one embodiment, the formulations of the present disclosure can contain two oil phases: a mixture of lidocaine and tetracaine, e.g. eutectic mixture of lidocaine and tetracaine, and petrolatum. The use of an emulsifying agent or combination of emulsifying agents that can properly emulsify all the oil phases can be significant. Hydrophile-lipophile balance number (HLB number) is a notable parameter that can be used in characterizing emulsifying agents.

It has been discovered that emulsifying agents having HLB values of 6.7 or greater do not properly emulsify certain formulations of the present disclosure, unless the water to polyvinyl alcohol ratio is increased. In some embodiments, it has been discovered that in certain formulations of the current disclosure, Span 40 (Sorbitan monopalmitate, HLB 6.7) does not adequately emulsify the petrolatum for long periods of time, e.g., separation occurs. That being said, it has been discovered that emulsifiers having HLB values less than 6.7 (which excludes Span 40), and in particular, those with HLB values of less than 5, such as Span 60, (Sorbitan monostearate, HLB 4.7), as well as some other emulsifying agents with HLB numbers lower than 6.7, can properly emulsify both the eutectic mixture and petrolatum. Non-limiting examples of such effective emulsifying agents can include Glyceryl monostearate (HLB number 3.8), Sorbitan sesquioleate (HLB number 3.7), Span 65 (Sorbitan tristearate, HLB number 2.1), and Span 80 (Sorbitan monooleate, HLB number 4.3).

The formulations of the present disclosure are for pain control and can be used to treat a variety of pains and their sources. In one embodiment, the formulation can be used to treat neuropathic pain. Typically, the formulations of the present disclosure can provide relief from pain, e.g. neuropathic pain and post herpetic neuralgia, within about 60 minutes, about 45 minutes, or even in as short of a time as within about 30 minutes after application to a skin surface proximate the pain. In order for the solid-forming local anesthetic formulation to provide significant relief of the pain, it is generally desirable that the formulation remain on the skin surface of the subject for a period of at least about 20 minutes. When the pain being treated is neuropathic pain, the source or underlying cause of the neuropathic pain being treated can vary. Non-limiting examples of causes of neuropathic pain include diabetic neuropathies and pain associated with postsurgical/post-traumatic conditions. Once applied, the solid-forming local anesthetic formulations of the present disclosure can be left on the skin surface, either as the semi-solid or as the soft coherent solid, for extended periods of time. After sufficient water evaporation, the semi-solid will form a soft coherent solid that can be removed from the skin as a solid, e.g., unlike in the initial state that has more of a liquid or pasty consistency that can be removed by simple wiping, the soft coherent solid can be removed as a solid piece or just a few solid pieces once transformed from semi-solid to solid.

EXAMPLES

The following examples illustrate the embodiments of the disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be the most practical embodiments of the disclosure.

Example 1—Viscosity Testing of the Formulations

The following outlines the testing procedures for measuring the viscosity of formulations of the present disclosure.

1. The samples to be tested are removed from the refrigerator and allow them to equilibrate to room temperature (about 25° C.) for at least 1 hour before handling.

2. Using a balance, place the empty small sample adapter (13R) on the balance, and press the tare button. Once the adapter has been tared, fill it with sample material to approximately ⅓ of the total weight (about 7 grams). Tap the adapter on a hard surface for several seconds to remove any entrapped air that might be present in the bottom. Continue to fill the sample adapter ⅓ at a time with additional sample material while tapping to remove entrapped air until the sample weight is 20 to 21 grams (maximum).

3. Using a balance centrifuge, spin the sample in the adapter for approximately 30 seconds at a high speed (approximately 4000 rpm) in order to remove any additional air bubbles within the sample.

4. After centrifuging, add additional sample material (about 1 gram) to obtain a final sample weight that is 21 to 22 grams. Record the sample weight (in grams).

5. Set the temperature controller on the viscometer to 23±2° C. Equilibrate the sample in the small sample adapter. Using a thermometer, insert the probe no more than 1 cm into the center of the sample, away from the adapter walls.

6. The sample is now ready to be tested on the viscometer. Insert the sample adapter into the sample adapter holder, align the groove, and lock into place. Remove the back holder supporting the sample adapter by unscrewing the nut located behind the spindle coupling nut module. Align the spindle coupling link with the viscometer coupling nut, and rotate the spindle clockwise. Replace the back holder, submerging the spindle in the middle of the sample holder at the same time. Avoid sample perturbation as much as possible. Screw the nut maintaining the back adapter behind the spindle coupling nut module. The spindle should be immersed in the sample up to the middle of the shaft indentation for the viscosity measurement. Failure to immerse the spindle up to the middle of the shaft indentation could result in a faulty viscosity reading.

7. Once the spindle is firmly in place, press the "SET SPEED" key once, and use the t or j arrows to set the spindle speed to 4.0 rpm. Press the "SET SPEED" key again. Once the proper speed (4.0 rpm) and spindle (7) are shown in the display, set the timer to countdown from 2 minutes.

8. Simultaneously start the timer and press the "MOTOR ON/OFF" key to begin the viscosity measurement. Allow the reading to equilibrate for 2 minutes before recording the viscosity reading and % torque value.

9. If the reading is out of the viscometer's range (% torque reading>100.0%), the cp and torque reading will display EEEE. At this point, turn off the motor, change the speed to the next lowest setting, and re-start the timer for 2 minutes. Turn the motor and timer on simultaneously, and allow the reading to equilibrate for 2 minutes before recording the torque and viscosity values. If the torque and viscosity are still out-of-range (EEEE) continue to incrementally reduce the speed, and re-run the sample until % T and viscosity values are in range.

10. After an equilibration time of 2 minutes has elapsed, record the % torque and viscosity values. Press the motor key off. At this point, unlock and carefully remove the sample adapter from the sample adapter holder. Remove the spindle from the viscometer by holding the viscometer coupling nut and rotating the spindle counter clockwise.

11. Remove the excess sample material from the spindle. The remaining sample in the sample adapter can be placed in the waste container.

Example 2

The viscosity of the formulation primarily impacts the difficulty of squeezing the product out of the tube and spreading the product on the skin. Lower viscosities are easier for both expulsion out of their containers and application to the skin, however formulations with overly low viscosities may drip excessively out of the tube or run after application to the skin.

Several formulations were produced with varying viscosities and have demonstrated various viscosity ranges. The following formulations were produced and evaluated for wear properties. Formulation 1 with a viscosity of ~28k centipoise was easy to apply and spread, but was somewhat runny. Formulations 2 and 3 showed slightly higher viscosities along with decreased tendency to run. Formulations 4 and 5 had yet higher viscosities, but were still easy to squeeze from the tube and very easily spread in a flat layer. These higher viscosity formulations showed lower tendency to run. Formulation 6 with a viscosity of ~828k was noticeably thicker and needed more effort to dispense and spread, but was still suitable for use for some applications, but would be less desirable for very sensitive skin surfaces, such as skin surfaces suffering from allodynia.

| Formulation | 1 | 2 | 3 | 3A | 3B | 4 | 5 | 6 |
|---|---|---|---|---|---|---|---|---|
| Viscosity (cP) | 28,460 | 47,800 | 67,800 | 79,500 | 122,500 | 370,500 | 454,500 | 828,500 |
| Ingredients | | | | | | | | |
| Lidocaine (base) | 7.00% | 7.00% | 7.00% | 7.00% | 7.00% | 7.00% | 7.00% | 7.00% |
| Tetracaine (base) | 7.00% | 7.00% | 7.00% | 7.00% | 7.00% | 7.00% | 7.00% | 7.00% |
| Purified Water | 54.27% | 37.94% | 51.87% | 39.94% | 35.94% | 35.94% | 25.94% | 25.94% |
| DiCalcium Phosphate | — | 24.00% | — | 18.00% | 27.00% | 27.00% | 36.00% | 36.00% |
| Polyvinyl Alcohol | 21.60% | 12.00% | 24.00% | 14.00% | 14.00% | 14.00% | 12.00% | 12.00% |
| White Petrolatum | 8.00% | 10.00% | 8.00% | 10.00% | 5.00% | 5.00% | 10.00% | 10.00% |
| Span 40 (Sorbitan Monopalmitate) | 2.00% | 2.00% | 2.00% | — | — | 4.00% | 2.00% | 2.00% |
| Span 60 (Sorbitan Monostearate) | — | — | — | 4.00% | 4.00% | — | — | — |
| Methylparaben | 0.10% | 0.05% | 0.10% | 0.05% | 0.05% | 0.05% | 0.05% | 0.05% |
| Propylparaben | 0.03% | 0.01% | 0.03% | 0.01% | 0.01% | 0.01% | 0.01% | 0.01% |
| Total | 100% | 100% | 100% | 100% | 100% | 100% | 100% | 100% |

Example 3

The total water content of the formulation is significant from the standpoint of chemical stability and drying time. It has been shown that in aqueous solutions, tetracaine hydrolyzes to 4-butylaminobenzoic acid (4-BABA) and 2-dimethylaminoethanol (DMAE). Thus, degradation products in the formulation should be minimized in order to ensure optimal potency and purity of the formulation. Studies of various formulations (see table below) have shown that the levels of 4-BABA in the formulation correlate to the total water content in the formulation. In the sense that it is desirable to maintain levels of 4-BABA below 3% after 24 months of storage at 5° C. (shelf-life), for example, it would be desirable to ensure total water content remains below ~50%.

| | Formulation | | | | |
|---|---|---|---|---|---|
| | 7 | 8 | 9 | 10 | 11 |
| Water Content | 29.54% | 31.94% | 42.82% | 48.88% | 51.87% |
| 4-BABA level after 12 months storage at 5° C. | 0.75% | 0.82% | 1.09% | 1.42% | 1.50% |
| Projected 4-BABA level after 24 months storage at 5° C. | 1.50% | 1.64% | 2.18% | 2.84% | 3.00% |
| Ingredients | | | | | |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 29.54% | 31.94% | 42.82% | 48.88% | 51.87% |
| DiCalcium Phosphate | 32.40% | 30.00% | — | — | — |
| Polyvinyl Alcohol | 12.00% | 12.00% | 19.77% | 27.00% | 24.00% |
| White Petrolatum | 10.00% | 10.00% | — | 8.00% | 8.00% |
| Span 40 (Sorbitan Monopalmitate) | 2.00% | 2.00% | 3.30% | 2.00% | 2.00% |
| Methylparaben | 0.05% | 0.05% | 0.09% | 0.10% | 0.10% |
| Propylparaben | 0.01% | 0.01% | 0.02% | 0.02% | 0.03% |
| Corn Starch | — | — | 20.00% | — | — |
| Total | 100% | 100% | 100% | 100% | 100% |

Since the evaporation of water causes the formulation to form a solidified layer, it is expected that total water content will directly impact drying time. Several formulations were studied to assess the impact of water content on drying time, and the results provided below indicate that a formulation with ~30% water was completely dry to the touch in approximately 10 minutes, whereas formulations with 40% and 54% water needed approximately 30 and 60 minutes, respectively, to be dry to the touch. Dry to the touch means the surface of the formulation layer is solidified enough so that a light touch by a finger does not remove any formulation from the layer.

| | Formulation | | |
|---|---|---|---|
| | 12 | 13 | 14 |
| Water Content | 31.94% | 39.94% | 54.27% |
| Drying Time | Less than 10 minutes | Between 10-30 minutes | Between 30-60 minutes |
| Ingredients | | | |
| Lidocaine (base) | 7.00% | 7.00% | 7.00% |
| Tetracaine (base) | 7.00% | 7.00% | 7.00% |
| Purified Water | 31.94% | 39.94% | 54.27% |
| DiCalcium Phosphate | 30.00% | 18.00% | — |
| Polyvinyl Alcohol | 12.00% | 14.00% | 21.60% |
| White Petrolatum | 10.00% | 10.00% | 8.00% |
| Span 40 (Sorbitan Monopalmitate) | 2.00% | — | 2.00% |
| Span 60 (Sorbitan Monostearate) | — | 4.00% | — |
| Methylparaben | 0.05% | 0.05% | 0.10% |
| Propylparaben | 0.01% | 0.01% | 0.03% |
| Total | 100% | 100% | 100% |

Example 4

Since the formulations herein may be stored in refrigerated conditions, the impact of freezing or cycling temperatures (freeze-thaw) on the formulations is considered. Freeze-thaw cycles may cause the PVA molecules in the formulations to crosslink, resulting in a dramatic increase in viscosity which may make the formulation difficult to spread on skin or even remove from an application tube. A series of cycling (freeze-thaw) studies was performed on several formulations in order to assess the impact of exposure to multiple "freeze-thaw" cycles. One freeze-thaw cycle is defined as exposure to freezing conditions (e.g., −18° C. to 22° C.) for 48 hours followed by exposure to room temperature thawing conditions (e.g., about 25° C.) for 48 hours. A more robust formulation will show less increase in viscosity after exposure to multiple freeze-thaw cycles. It is noted that exceeding the 48 hour time periods for freezing and thawing for a short period of time will typically not impact the test results. Several formulations have been developed and subjected to freeze-thaw cycles. Viscosity at baseline and after each freeze-thaw cycle was measured using the method outlined in Example 1.

The data gathered on the formulations below indicate that the water to PVA ratio has an impact on the resistance to freeze/thaw exposures. Formulations having a water:PVA ratio greater than 2.5 demonstrated less pronounced viscosity increases after exposure to multiple freeze/thaw cycles, as shown in the table below.

|  | Formulation | | | | |
|---|---|---|---|---|---|
|  | 15 | 16 | 17 | 18 | 19 |
| Water/PVA ratio | 2.16 | 2.46 | 2.57 | 2.85 | 3.16 |
| Ingredients |  |  |  |  |  |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 25.94% | 29.54% | 35.94% | 39.94% | 37.94% |
| DiCalcium Phosphate | 36.00% | 32.40% | 27.00% | 18.00% | 24.00% |
| Polyvinyl Alcohol | 12.00% | 12.00% | 14.00% | 14.00% | 12.00% |
| White Petrolatum | 10.00% | 10.00% | 5.00% | 10.00% | 10.00% |
| Span 40 (Sorbitan Monopalmitate) | 2.00% | 2.00% | — | — | 2.00% |
| Span 60 Sorbitan Monostearate) | — | — | 4.00% | 4.00% | — |
| Methylparaben | 0.05% | 0.05% | 0.05% | 0.05% | 0.05% |
| Propylparaben | 0.01% | 0.01% | 0.01% | 0.01% | 0.01% |
| Total | 100% | 100% | 100% | 100% | 100% |
| Initial Viscosity | 454,500 | 146,000 | 122,500 | 79,500 | 47,800 |
| Freeze/Thaw | Viscosity Results | | | | |
| 1 cycle | 7,200,000 | 436,500 | 170,000 | 94,500 | 29,440 |
| 2 cycles | >8,000,000 | 427,000 | 226,500 | 114,000 | 29,160 |
| 3 cycles | >8,000,000 | 1,150,000 | 210,000 | 146,000 | 33,080 |
| 4 cycles | >8,000,000 | 2,385,000 | 227,500 | 87,000 | 46,400 |
| 5 cycles | >8,000,000 | 3,310,000 | 333,000 | 137,500 | 38,000 |
| Freeze/Thaw | Viscosity Increase Multiple | | | | |
| 1 cycle | 16 | 3 | 1 | 1 | 1 |
| 2 cycles | >18 | 3 | 2 | 1 | 1 |
| 3 cycles | >18 | 8 | 2 | 2 | 1 |
| 4 cycles | >18 | 16 | 2 | 1 | 1 |
| 5 cycles | >18 | 23 | 3 | 2 | 1 |

|  | Formulation | |
|---|---|---|
|  | 20 | 21 |
| Purified Water | 35.94% | 35.94% |
| DiCalcium Phosphate | 27.00% | 27.00% |
| Polyvinyl Alcohol | 14.00% | 14.00% |
| White Petrolatum | 5.00% | 5.00% |
| Span 40 (Sobitan Monopalmitate) | 4.00% | — |
| Span 60 (Sorbitan Monostearate) | — | 4.00% |
| Methylparaben | 0.05% | 0.05% |
| Propylparaben | 0.01% | 0.01% |
| Total | 100% | 100% |

Example 5

Two solid-forming local anesthetic formulations were made and their compositions are listed in the following table. The formulations are identical except Formulation 20 used Span 40 (Sobitan Monopalmitate) as emulsifying agent and Formulation 21 used Span 60 (Sorbitan Monostearate). After about three months, Formulation 20 showed significantly more phase separation that Formulation 21.

|  | Formulation | |
|---|---|---|
|  | 20 | 21 |
| Ingredients |  |  |
| Lidocaine | 7.00% | 7.00% |
| Tetracaine | 7.00% | 7.00% |
| Initial Viscosity | 132,000 | 122,500 |
| Water/PVA ratio | 2.57 | 2.57 |

Example 6

Three solid-forming local anesthetic formulations were made and their compositions are listed in the following table. The formulations were identical except that the emulsifying agents were different: Span 65 (Sorbitan tristearate, HLB number 2.1) was used in formulation 31, Span 80 (Sorbitan monooleate, HLB number 4.3) was used in Formulation 32, and Span 85 (Sorbitan trioleate, HLB number 1.8) was used in Formulation 33. After about three weeks, none of the formulations showed detectable phase separation.

|  | Formulation Number | | |
| --- | --- | --- | --- |
|  | 22 | 23 | 24 |
| Ingredients | | | |
| Lidocaine | 7.00% | 7.00% | 7.00% |
| Tetracaine | 7.00% | 7.00% | 7.00% |
| Purified Water | 35.94% | 35.94% | 35.94% |
| DiCalcium Phosphate | 27.00% | 27.00% | 27.00% |
| Polyvinyl Alcohol | 14.00% | 14.00% | 14.00% |
| White Petrolatum | 5.00% | 5.00% | 5.00% |
| Sorbitan tristearate (Span 65) | 4.00% | | |
| Sorbitan monooleate, (Span 80) | | 4.00% | |
| Sorbitan trioleate (Span 85) | | | 4.00% |
| Methylparaben | 0.05% | 0.05% | 0.05% |
| Propylparaben | 0.01% | 0.01% | 0.01% |
| Water/PVA ratio | 2.57 | 2.57 | 2.57 |

While the invention has been described with reference to certain embodiments, those skilled in the art will appreciate that various modifications, changes, omissions, and substitutions can be made without departing from the spirit of the disclosure. It is therefore intended that the invention be limited only by the scope of the appended claims.

What is claimed is:

1. A formulation for pain control, comprising:
   from about 4 wt % to about 10 wt % lidocaine;
   from about 4 wt % to about 10 wt % tetracaine;
   from about 10 wt % to about 18 wt % polyvinyl alcohol;
   from about 2 wt % to about 6 wt % of an emulsifier selected from sorbitan monopalmitate or sorbitan monostearate;
   from about 25.94 wt % to about 51.87 wt % water;
   from about 2 wt % to about 13 wt % petrolatum; and
   from about 18 wt % to about 36 wt % dicalcium phosphate;
   wherein the formulation has an initial viscosity that ranges from about 40,000 centipoise to 370,500 centipoise.

2. The formulation of claim 1, wherein the formulation has an initial viscosity of from 47,800 centipoise to 370,500 centipoise.

3. The formulation of claim 1, wherein the formulation comprises 7 wt % of the lidocaine and 7 wt % of the tetracaine.

4. The formulation of claim 1, wherein the lidocaine and the tetracaine are present in the formulation at a weight ratio ranging from 2:1 to 1:2.

5. The formulation of claim 1, wherein the polyvinyl alcohol has an average molecular mass ranging from 20,000 daltons to 100,000 daltons.

6. The formulation of claim 1, wherein the polyvinyl alcohol has an average molecular mass ranging from 30,000 daltons to 80,000 daltons.

7. The formulation of claim 1, wherein the lidocaine and tetracaine comprise a eutectic mixture.

8. The formulation of claim 1, wherein the emulsifying agent is sorbitan monopalmitate.

9. The formulation of claim 1, wherein the emulsifying agent is sorbitan monostearate.

10. The formulation of claim 1, wherein the formulation is for application to a skin surface.

11. The formulation of claim 1, wherein the lidocaine and the tetracaine are each in their base form.

12. The formulation of claim 1, wherein the formulation has an increase in viscosity after 3 freeze-thaw cycles of 8 times or less the initial viscosity, each of the 3 freeze-thaw cycles being determined by placement of the formulation in an environment of −18° C. to −22° C. for a period of time of 48 hours followed by thawing of the formulation at room temperature (about 25° C.) for a period of 48 hours.

13. The formulation of claim 1, wherein the formulation has an initial viscosity of at least 50,000 centipoise and has an increase in viscosity after 3 freeze-thaw cycles of less than 8 times the initial viscosity with a maximum viscosity of 1,500,000 centipoise, each of the 3 freeze-thaw cycles being determined by placement of the formulation in an environment of −18° C. to −22° C. for a period of time of 48 hours followed by thawing of the formulation at room temperature (about 25° C.) for a period of 48 hours.

14. The formulation of claim 1, wherein the formulation has an initial viscosity of at least 50,000 centipoise and has an increase in viscosity after 3 freeze-thaw cycles of less than 5 times the initial viscosity with a maximum viscosity of 1,500,000 centipoise, each of the 3 freeze-thaw cycles being determined by placement of the formulation in an environment of −18° C. to −22° C. for a period of time of 48 hours followed by thawing of the formulation at room temperature (about 25° C.) for a period of 48 hours.

* * * * *